US011713483B2

(12) United States Patent
Wong et al.

(10) Patent No.: US 11,713,483 B2
(45) Date of Patent: Aug. 1, 2023

(54) METHOD FOR DETECTION OF ANALYTES VIA POLYMER COMPLEXES

(71) Applicant: Children's Medical Center Corporation, Boston, MA (US)

(72) Inventors: Wesley Philip Wong, Cambridge, MA (US); Clinton H. Hansen, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 690 days.

(21) Appl. No.: 16/074,952

(22) PCT Filed: Feb. 8, 2017

(86) PCT No.: PCT/US2017/017058
§ 371 (c)(1),
(2) Date: Aug. 2, 2018

(87) PCT Pub. No.: WO2017/139409
PCT Pub. Date: Aug. 17, 2017

(65) Prior Publication Data
US 2019/0048409 A1 Feb. 14, 2019

Related U.S. Application Data

(60) Provisional application No. 62/293,306, filed on Feb. 9, 2016.

(51) Int. Cl.
| | | |
|---|---|---|
| *C12Q 1/6848* | (2018.01) | |
| *C12Q 1/6876* | (2018.01) | |
| *G01N 33/53* | (2006.01) | |
| *C12Q 1/68* | (2018.01) | |

(52) U.S. Cl.
CPC ............ *C12Q 1/6848* (2013.01); *C12Q 1/68* (2013.01); *C12Q 1/6876* (2013.01); *G01N 33/5306* (2013.01); *G01N 33/5308* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,571,677 A | 11/1996 | Gryaznov | |
| 5,635,352 A | 6/1997 | Urdea et al. | |
| 5,888,731 A | 5/1999 | Yager et al. | |
| 5,902,724 A | 5/1999 | Lane et al. | |
| 6,143,504 A | 11/2000 | Das et al. | |
| 6,232,066 B1 | 5/2001 | Felder et al. | |
| 6,251,660 B1 | 6/2001 | Muir et al. | |
| 6,569,306 B1 | 5/2003 | Read et al. | |
| 6,770,698 B1 | 8/2004 | Chu et al. | |
| 8,491,454 B2 | 7/2013 | Wong et al. | |
| 8,795,143 B2 | 8/2014 | Wong et al. | |
| 9,255,905 B1 | 2/2016 | Mellors et al. | |
| 9,914,958 B2 | 3/2018 | Wong et al. | |
| 9,994,839 B2 | 6/2018 | Lo et al. | |
| 10,919,037 B2 | 2/2021 | Wong et al. | |
| 10,948,401 B2 | 3/2021 | Yang et al. | |
| 11,198,900 B2 | 12/2021 | Koussa et al. | |
| 11,396,650 B2 | 7/2022 | Wong et al. | |
| 2002/0182717 A1 | 12/2002 | Karlsson et al. | |
| 2003/0143549 A1 | 7/2003 | Yang et al. | |
| 2003/0186301 A1 | 10/2003 | Christian et al. | |
| 2006/0194240 A1* | 8/2006 | Arnold, Jr. ........... | C12Q 1/6816 435/6.1 |
| 2006/0257958 A1 | 11/2006 | Bruno | |
| 2007/0026423 A1 | 2/2007 | Koehler et al. | |
| 2007/0037152 A1 | 2/2007 | Drmanac | |
| 2007/0117109 A1 | 5/2007 | Rothemund | |
| 2007/0154899 A1 | 7/2007 | Coull et al. | |
| 2008/0038725 A1 | 2/2008 | Luo et al. | |
| 2008/0131870 A1 | 6/2008 | Allawi et al. | |
| 2008/0312103 A1 | 12/2008 | Nemoto et al. | |
| 2009/0087838 A1 | 4/2009 | Reif et al. | |
| 2009/0286694 A1 | 11/2009 | Zainiev et al. | |
| 2010/0015608 A1 | 1/2010 | Kolpashchikov | |
| 2010/0035247 A1 | 2/2010 | Burton | |
| 2010/0206730 A1 | 8/2010 | Hunkapiller et al. | |
| 2010/0216658 A1 | 8/2010 | Chaput et al. | |
| 2011/0086774 A1 | 4/2011 | Dunaway | |
| 2011/0268654 A1 | 11/2011 | Hilderbrand et al. | |
| 2013/0004523 A1 | 1/2013 | Zubarev et al. | |
| 2013/0130884 A1 | 5/2013 | Wong et al. | |
| 2013/0196341 A1 | 8/2013 | Neely et al. | |
| 2013/0310260 A1 | 11/2013 | Kim et al. | |
| 2013/0344508 A1 | 12/2013 | Schwartz et al. | |
| 2014/0255939 A1 | 9/2014 | Wong et al. | |
| 2014/0284213 A1 | 9/2014 | Sabin et al. | |
| 2014/0302532 A1* | 10/2014 | Wilson ............... | G01N 33/6896 435/7.92 |

(Continued)

FOREIGN PATENT DOCUMENTS

| | | |
|---|---|---|
| JP | H06-508753 A | 10/1994 |
| JP | 2000-312589 A | 8/2000 |
| JP | 2003-219897 A | 8/2003 |
| JP | 2005-536234 A | 12/2005 |
| JP | 2008-259453 A | 10/2008 |
| JP | 2009-521230 | 6/2009 |

(Continued)

OTHER PUBLICATIONS

Invitation to Pay Additional Fees for PCT/US2017/017058 dated Mar. 28, 2017.
International Search Report and Written Opinion for PCT/US2017/017058 dated May 31, 2017.
International Preliminary Report on Patentability dated Aug. 23, 2018 for PCT/US2017/017058.

(Continued)

*Primary Examiner* — Ann Montgomery
(74) *Attorney, Agent, or Firm* — Wolf, Greenfield & Sacks, P.C.

(57) ABSTRACT

Provided herein are products and methods for detecting analytes using polymers that bind to such analytes and thereby undergo a conformational change or contribute to a newly formed complex.

21 Claims, 3 Drawing Sheets

(56) References Cited

U.S. PATENT DOCUMENTS

| | | |
|---|---|---|
| 2015/0027894 A1 | 1/2015 | Puleo et al. |
| 2015/0093836 A1 | 4/2015 | Suzuki et al. |
| 2015/0099650 A1 | 4/2015 | Sood et al. |
| 2015/0361422 A1 | 12/2015 | Sampson et al. |
| 2016/0186238 A1 | 6/2016 | Liu et al. |
| 2017/0369935 A1 | 12/2017 | Koussa et al. |
| 2018/0135043 A1 | 5/2018 | Wong et al. |
| 2018/0223344 A1 | 8/2018 | Chandrasekaran et al. |
| 2018/0291434 A1 | 10/2018 | Wong et al. |
| 2019/0070604 A1 | 3/2019 | Wong et al. |
| 2020/0116712 A1 | 4/2020 | Hansen et al. |
| 2020/0340033 A1 | 10/2020 | Wong et al. |
| 2021/0239602 A1 | 8/2021 | Yang et al. |

FOREIGN PATENT DOCUMENTS

| | | |
|---|---|---|
| WO | WO 93/01313 A1 | 1/1993 |
| WO | WO 98/18961 A1 | 5/1998 |
| WO | WO 00/40751 A2 | 7/2000 |
| WO | WO 2004/016767 A2 | 2/2004 |
| WO | WO 2007/076128 A2 | 7/2007 |
| WO | WO 2011/005221 A1 | 1/2011 |
| WO | WO 2011/153211 A1 | 12/2011 |
| WO | WO 2012/058638 A2 | 5/2012 |
| WO | WO 2013/010023 A2 | 1/2013 |
| WO | WO 2013/067489 A1 | 5/2013 |
| WO | WO 2014/011800 A1 | 1/2014 |
| WO | WO 2015/006626 A1 | 1/2015 |
| WO | WO 2015/040009 A1 | 3/2015 |
| WO | WO 2015/164602 A2 | 10/2015 |
| WO | WO 2016/089588 A1 | 6/2016 |
| WO | WO 2016/196824 A1 | 12/2016 |
| WO | WO 2017/003950 A2 | 1/2017 |
| WO | WO 2017/139409 A1 | 8/2017 |
| WO | WO 2017/147398 A1 | 8/2017 |
| WO | WO 2018/106721 A1 | 6/2018 |
| WO | WO 2019/100080 A1 | 5/2019 |

OTHER PUBLICATIONS

[No Author Listed], Wikipedia Entry, "XhoI." May 14, 2014. Retrieved from the internet. <https://en.wikipedia.org/w/index.php?title=XhoI&oldid=608536958>. Retrieved on Oct. 18, 2016.

Aaij et al., The gel electrophoresis of DNA. Biochim Biophys Acta. May 10, 1972;269(2):192-200.

Bellot et al., Recovery of intact DNA nanostructures after agarose gel-based separation. Nat Methods. Mar. 2011;8(3):192-4. doi: 10.1038/nmeth0311-192.

Bishop et al., Electrophoretic separation of viral nucleic acids on polyacrylamide gels. J Mol Biol. Jun. 28, 1967;26(3):373-87.

Bustamante et al., Entropic elasticity of lambda-phage DNA. Science. Sep. 9, 1994;265(5178):1599-600.

Bustamante et al., Ten years of tension: single-molecule DNA mechanics. Nature. Jan. 23, 2003;421(6921):423-7.

Butko et al., Detection of Ligand-Induced Conformational Changes in Oligonucleotides by Second-Harmonic Generation at a Supported Lipid Bilayer Interface. Anal Chem. Nov. 1, 2016;88(21):10482-10489. Epub Oct. 12, 2016. Accepted Manuscript, 23 pages.

Chandrasekaran et al., Label-free Detection of Specific Nucleic Acid Sequences using DNA Nanoswitches. The RNA Institute, University at Albany, State University of New York.

Chandrasekaran et al., Programmable DNA Nanoswitches for Detection of Nucleic Acid Sequences. ACS Sens., 2016, 1 (2), pp. 120-123.

Cheng et al., Early pregnancy factor in cervical mucus of pregnant women. Am J Reprod Immunol. Feb. 2004;51(2):102-5.

Chilkoti et al., Molecular Origins of the Slow Streptavidin-Biotin Dissociation Kinetics. J Am Chem Soc. 1995;117(43):10622-8.

Chivers et al., A streptavidin variant with slower biotin dissociation and increased mechanostability. Nat Methods. May 2010;7(5):391-3. doi: 10.1038/nmeth.1450. Epub Apr. 11, 2010.

Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.

Conde et al., Implantable hydrogel embedded dark-gold nanoswitch as a theranostic probe to sense and overcome cancer multidrug resistance. Proc Natl Acad Sci U S A. Mar. 17, 2015;112(11):E1278-87. doi: 10.1073/pnas.1421229112. Epub Mar. 2, 2015.

Deniz et al., Single-molecule biophysics: at the interface of biology, physics and chemistry. J R Soc Interface. Jan. 6, 2008;5(18):15-45.

Doshi et al., In vitro nanobody discovery for integral membrane protein targets. Sci Rep. Oct. 24, 2014;4:6760. doi: 10.1038/srep06760.

Douglas et al., A logic-gated nanorobot for targeted transport of molecular payloads. Science. Feb. 17, 2012;335(6070):831-4. doi: 10.1126/science.1214081.

Douglas et al., Self-assembly of DNA into nanoscale three-dimensional shapes. Nature. May 21, 2009;459(7245):414-8. doi: 10.1038/nature08016.

Evans et al., Dynamic strength of molecular adhesion bonds. Biophys J. Apr. 1997;72(4):1541-55.

Evans et al., Forces and bond dynamics in cell adhesion. Science. May 25, 2007;316(5828):1148-53.

Evans, Probing the relation between force—lifetime—and chemistry in single molecular bonds. Annu Rev Biophys Biomol Struct. 2001;30:105-28.

França et al., A review of DNA sequencing techniques. Q Rev Biophys. May 2002;35(2):169-200.

Green, Avidin and streptavidin. Methods Enzymol. 1990;184:51-67.

Greenleaf et al., High-resolution, single-molecule measurements of biomolecular motion. Annu Rev Biophys Biomol Struct. 2007;36:171-90.

Halvorsen et al., Binary DNA nanostructures for data encryption. PLoS One. 2012;7(9):e44212. doi: 10.1371/journal.pone.0044212. Epub Sep. 11, 2012.

Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.

Halvorsen et al., Massively Parallel Single-Molecule Manipulation Using Centrifugal Force. Biophys J. Jun. 2, 2010;98(11):L53-5.

Halvorsen et al., Nanoengineering a single-molecule mechanical switch using DNA self-assembly. Nanotechnology. Dec. 9, 2011;22(49):494005. doi:10.1088/0957-4484/22/49/494005. Epub Nov. 21, 2011.

Halvorsen, Probing Weak Single-Molecule Interactions: Development and Demonstration of a New Instrument. Boston University, College of Engineering dissertation. 2007: 102 pages.

Hanke et al., Entropy loss in long-distance DNA looping. Biophys J. Jul. 2003;85(1):167-73.

Hansen et al., Nanoswitch-linked immunosorbent assay (NLISA) for fast, sensitive, and specific protein detection. PNAS. Sep. 26, 2017;114(39):10367-10372. Supporting Information, 4 pages.

Hassur et al., UV shadowing—a new and convenient method for the location of ultraviolet-absorbing species in polyacrylamide gels. Anal Biochem. May 1974;59(1):162-4.

Hellman et al., Electrophoretic mobility shift assay (EMSA) for detecting protein-nucleic acid interactions. Nat Protoc. 2007;2(8):1849-61.

Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.

Jones et al, Nanomaterials. Programmable materials and the nature of the DNA bond. Science. Feb. 20, 2015;347(6224):1260901. doi: 10.1126/science.1260901.

Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.

Khalil et al., Single M13 bacteriophage tethering and stretching. Proc Natl Acad Sci U S A. Mar. 20, 2007;104(12):4892-7. Epub Mar. 13, 2007.

Kim et al., A mechanically stabilized receptor-ligand flex-bond important in the vasculature. Nature. Aug. 19, 2010;466(7309):992-5. doi: 10.1038/nature09295.

(56) References Cited

OTHER PUBLICATIONS

Klumb et al., Energetic roles of hydrogen bonds at the ureido oxygen binding pocket in the streptavidin-biotin complex. Biochemistry. May 26, 1998;37(21):7657-63.
Koch et al., Prospects and limitations of the rosette inhibition test to detect activity of early pregnancy factor in the pig. J Reprod Fertil. May 1985;74(1):29-38.
Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.
Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.
Kufer et al., Single-molecule cut-and-paste surface assembly. Science. Feb. 1, 2008;319(5863):594-6. doi:10.1126/science.1151424.
Leier et al., Cryptography with DNA binary strands. Biosystems. Jun. 2000;57(1):13-22.
Mcdonell et al., Analysis of restriction fragments of T7 DNA and determination of molecular weights by electrophoresis in neutral and alkaline gels. J Mol Biol. Feb. 15, 1977;110(1):119-46.
Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.
Morton et al., Rosette inhibition test: A multicentre investigation of early pregnancy factor in humans. J Reprod Immunol. Sep. 1982;4(5):251-61.
Morton et al., Early pregnancy factor. Semin Reprod Endocrinol. May 1992;10:72-82.
Neuman et al., Single-molecule force spectroscopy: optical tweezers, magnetic tweezers and atomic force microscopy. Nat Methods. Jun. 2008;5(6):491-505. doi: 10.1038/nmeth.1218.
Park et al., Dual blockade of cyclic AMP response element-(CRE) and AP-1-directed transcription by CRE-transcription factor decoy oligonucleotide. gene-specific inhibition of tumor growth. J Biol Chem. Jan. 15, 1999;274(3):1573-80.
Pei et al, A DNA nanostructure-based biomolecular probe carrier platform for electrochemical biosensing. Adv Mater. Nov. 9, 2010;22(42):4754-8. doi: 10.1002/adma.201002767.
Quek et al., Mechanically controlled binary conductance switching of a single-molecule junction. Nat Nanotechnol. Apr. 2009;4(4):230-4. doi:10.1038/nnano.2009.10. Epub Mar. 1, 2009.
Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.
Rothemund, Folding DNA to create nanoscale shapes and patterns. Nature. Mar. 16, 2006;440(7082):297-302.
Sacca et al., DNA origami: the art of folding DNA. Angew Chem Int Ed Engl. Jan. 2, 2012;51(1):58-66. doi: 10.1002/anie.201105846. Epub Dec. 7, 2011.
Seeman, DNA in a material world. Nature. Jan. 23, 2003;421(6921):427-31.
Seeman, Nanomaterials based on DNA. Annu Rev Biochem. 2010;79:65-87. doi: 10.1146/annurev-biochem-060308-102244.
Shroff et al., Biocompatible force sensor with optical readout and dimensions of 6 nm3. Nano Lett. Jul. 2005;5(7):1509-14.
Shroff et al., Optical measurement of mechanical forces inside short DNA loops. Biophys J. Mar. 15, 2008;94(6):2179-86. Epub Dec. 7, 2007.
Smith et al., Overstretching B-DNA: the elastic response of individual double-stranded and single-stranded DNA molecules. Science. Feb. 9, 1996;271(5250):795-9.
Strunz et al., Dynamic force spectroscopy of single DNA molecules. Proc Natl Acad Sci U S A. Sep. 28, 1999;96(20):11277-82.
Su et al., Nucleic acid fluorescent probes for biological sensing. Appl Spectrosc. Nov. 2012;66(11):1249-62. doi: 10.1366/12-06803. Review.
Svoboda et al., Direct observation of kinesin stepping by optical trapping interferometry. Nature. Oct. 21, 1993;365(6448):721-7.
Thorne, Electrophoretic separation of polyoma virus DNA from host cell DNA. Virology. Jun. 1966;29(2):234-9.
Thuring et al., A freeze-squeeze method for recovering long DNA from agarose gels. Anal Biochem. May 26, 1975;66(1):213-20.
Wiita et al., Force-dependent chemical kinetics of disulfide bond reduction observed with single-molecule techniques. Proc Natl Acad Sci U S A. May 9, 2006;103(19):7222-7. Epub Apr. 27, 2006.
Winfree et al., Design and self-assembly of two-dimensional DNA crystals. Nature. Aug. 6, 1998;394(6693):539-44.
Wong et al., The effect of integration time on fluctuation measurements: calibrating an optical trap in the presence of motion blur. Opt Express. Dec. 11, 2006;14(25):12517-31.
Yang et al., Multiplexed single-molecule force spectroscopy using a centrifuge. Nat Commun. Mar. 17, 2016;7:11026(1-7). doi: 10.1038/ncomms11026.
Zadeh et al., Nupack: Analysis and design of nucleic acid systems. J Comput Chem. Jan. 15, 2011;32(1):170-3. doi: 10.1002/jcc.21596.
Zhang et al., Mechanoenzymatic cleavage of the ultralarge vascular protein, von Willebrand Factor. Science. Jun. 5, 2009;324(5932):1330-4.
Zheng et al., From molecular to macroscopic via the rational design of a self-assembled 3D DNA crystal. Nature. Sep. 3, 2009;461(7260):74-7. doi: 10.1038/nature08274.
Devaraj et al., Biomedical applications of tetrazine cycloadditions. Acc Chem Res. Sep. 20, 2011;44(9):816-27. doi: 10.1021/ar200037t. Epub May 31, 2011.
Hopwood et al., Integrated microfluidic system for rapid forensic DNA analysis: sample collection to DNA profile. Anal Chem. Aug. 15, 2010;82(16):6991-9. doi: 10.1021/ac101355r.
Kleiner et al., Small-molecule discovery from DNA-encoded chemical libraries. Chem Soc Rev. Dec. 2011;40(12):5707-17. doi: 10.1039/c1cs15076f. Epub Jun. 14, 2011.
Yang et al., An integratable microfluidic cartridge for forensic swab samples lysis. Forensic Sci Int Genet. Jan. 2014;8(1):147-58. doi: 10.1016/j.fsigen.2013.08.012. Epub Sep. 8, 2013.
Fang et al., Tuning surface states to achieve the modulated fluorescence of carbon dots for probing the activity of alkaline phosphatase and immunoassay of alpha-fetoprotein. Sensors and Actuators B: Chemical. 2018;257:620-628.
Lubken et al., Multiplexed Continuous Biosensing by Single-Molecule Encoded Nanoswitches. Nano Lett. Apr. 8, 2020;20(4):2296-2302. doi: 10.1021/acs.nanolett.9b04561. Epub Mar. 12, 2020.
Papadakis et al., Acoustic characterization of nanoswitch structures: application to the DNA Holliday Junction. Nano Lett. Dec. 8, 2010;10(12):5093-7. doi: 10.1021/nl103491v. Epub Nov. 1, 2010.
Ping, High Performing assay using antibody-conjugated DNA nanoswitches detects proteins. MRS Bulletin. 2017;42:780. 1 page.
Porchetta et al., Programmable Nucleic Acid Nanoswitches for the Rapid, Single-Step Detection of Antibodies in Bodily Fluids. J Am Chem Soc. Jan. 24, 2018;140(3):947-953. doi: 10.1021/jacs.7b09347. Epub Jan. 9, 2018.
Ando et al., Single-nanoparticle tracking with angstrom localization precision and microsecond time resolution. Biophys J. Dec. 18, 2018;115(12):2413-2427. Epub Nov. 17, 2018.
Baslé et al., Protein chemical modification on endogenous amino acids. Chem Biol. Mar. 26, 2010;17(3):213-27.
Cheezum et al., Quantitative comparison of algorithms for tracking single fluorescent particles. Biophys J. Oct. 2001;81(4):2378-88.
Fu et al., Flow-induced elongation of von Willebrand factor precedes tension-dependent activation. Nat Commun. Aug. 23, 2017;8(1):324.
Horn et al., Forks and combs and DNA: the synthesis of branched oligodeoxyribonucleotides. Nucleic Acids Res. Sep. 12, 1989;17(17):6959-67.
Jiang et al., Electrostatic steering enables flow-activated von willebrand factor to bind platelet glycoprotein, revealed by single-molecule stretching and imaging. J Mol Biol. Mar. 29, 2019;431(7):1380-1396. Epub Feb. 22, 2019.
Jiang et al., Stretching DNA to twice the normal length with single-molecule hydrodynamic trapping. Lab Chip. May 19, 2020;20(10):1780-1791.

(56) References Cited

OTHER PUBLICATIONS

Mendoza et al., Probing protein structure by amino acid-specific covalent labeling and mass spectrometry. Mass Spectrom Rev. Sep.-Oct. 2009;28(5):785-815.
Pinheiro et al., Challenges and opportunities for structural DNA nanotechnology. Nat Nanotechnol. Nov. 6, 2011;6(12):763-72.
Silver et al., Tethered-bead, immune sandwich assay. Biosens Bioelectron. Jan. 15, 2015;63:117-123. Epub Jul. 11, 2014.
Thompson et al., Precise nanometer localization analysis for individual fluorescent probes. Biophys J. May 2002;82(5):2775-83.
Ueno et al., Simple dark-field microscopy with nanometer spatial precision and microsecond temporal resolution. Biophys J. May 19, 2010;98(9):2014-23.
Van Oijen et al., Single-molecule kinetics of lambda exonuclease reveal base dependence and dynamic disorder. Science. Aug. 29, 2003;301(5637):1235-8.
Yang et al., Repurposing a Benchtop Centrifuge for High-Throughput Single-Molecule Force Spectroscopy. Methods Mol Biol. 2018;1665:353-366.

\* cited by examiner

METHOD FOR DETECTION OF ANALYTES VIA POLYMER COMPLEXES

RELATED APPLICATIONS

This application is a national stage filing under 35 U.S.C. 371 of International Application PCT/US2017/017058, filed Feb. 8, 2017, which was published under PCT Article 21(2) in English, and which claims the benefit under 35 U.S.C. § 119(e) of U.S. Provisional Application Ser. No. 62/293,306 filed on Feb. 9, 2016, entitled "METHOD FOR DETECTION OF ANALYTES VIA POLYMER COMPLEXES", the entire contents of each of which are incorporated by reference herein.

BACKGROUND OF INVENTION

Various clinical and non-clinical applications require analyte detection. Such analytes may be present in very low concentrations (or copies) and this poses a challenge to detection. In addition, some applications may benefit from the ability to detect not just a single analyte but a panel of analytes which together for a profile of a condition or predisposition to a condition. Assays intended for consumer use would similarly benefit from ease of use.

SUMMARY OF INVENTION

Provided herein are methods and compositions for use in detecting and quantifying analytes such as single compounds or complexes comprising two or more components. The methods and compositions are also useful for screening a plurality of compounds for those having a particular desired binding specificity.

These methods are achieved through the use of polymers, including polymer pairs, that are conjugated to binding partners of known or unknown specificity. The polymer pairs are designed so that both polymers in the pair bind to the same analyte, thereby converting from two separate, optionally linear polymers, into a complex in which the two polymers are effectively joined through the analyte. This newly formed complex is distinguishable from the linear forms of the polymers, and can be detected readily using any one of a variety of standard techniques including but not limited to gel electrophoresis. Additionally, combinations of polymer pairs may be used together, each specific for a different analyte, and each able to form upon binding analyte a complex that is distinguishable from complexes formed by other polymer pairs. Thus, the methods are amenable to multiplexed analysis, allowing detection and quantitation of a two or more analytes simultaneously.

Significantly, and unexpectedly, these methods are associated with lower noise, and thus higher signal to noise ratios, than some prior art detection techniques. The low noise of the method allows for sensitive detection of analytes or molecular interactions. This together with the relative ease in performing the assays and detecting the complexes and optionally their conformational changes renders these methods suitable for a variety of detecting and screening applications.

Thus, provided herein in one aspect is a method for detecting an analyte in a sample. The method comprises first combining a sample with a first polymer and a second polymer, each conjugated to an analyte-specific binding partner, under conditions that allow binding of analyte-specific binding partners to respective analytes, wherein the analyte-specific binding partners are able to bind to a single analyte simultaneously, and then detecting a complex formed by the binding of the first polymer and the second polymer to an analyte in the sample, wherein presence of the complex is indicative of presence of the analyte in the sample, and optionally wherein conformation of the complex identifies the analyte.

In some embodiments, the analyte-specific binding partners conjugated to the first and second polymers are identical. In some embodiments, the analyte-specific binding partners conjugated to the first and second polymers are different.

In some embodiments, one or both of the analyte-specific binding partners are antibodies. In some embodiments, one or both of the analyte-specific binding partners are antigen-binding antibody fragments.

In some embodiments, the analyte-specific binding partners bind to different epitopes of an analyte. In some embodiments, the analyte-specific binding partners bind to an identical epitope that is present at least twice in an analyte.

In some embodiments, one or both of the analyte-specific binding partners are aptamers.

In some embodiments, the analyte-specific binding partners are located at about the mid-point along the length of the first or second polymer.

In some embodiments, the first polymer and/or the second polymer is a nucleic acid. In some embodiments, the first polymer and/or the second polymer comprise naturally occurring nucleotides. In some embodiments, the first polymer and/or the second polymer comprise non-naturally occurring nucleotides. In some embodiments, the first polymer and/or the second polymer comprises M13 DNA, such as full-length or nearly full-length M13 DNA.

In some embodiments, the first polymer and/or the second polymer is a single-stranded nucleic acid. In some embodiments, the first polymer and/or the second polymer is a partially double-stranded nucleic acid. In some embodiments, the first polymer and/or the second polymer comprises a single-stranded nucleic acid hybridized to one or more oligonucleotides. In some embodiments, the one or more oligonucleotides have a total length about equal to the length of the single-stranded nucleic acid. In some embodiments, the one or more oligonucleotides have a total length about equal to 25%, 50% or 75% of the length of the single-stranded nucleic acid.

In some embodiments, the first polymer and/or the second polymer is a completely double-stranded nucleic acid.

In some embodiments, the first polymer and/or the second polymer is a completely double-stranded nucleic acid having nicks in at least one nucleic acid strand.

In some embodiments, the first polymer and/or the second polymer is a non-nucleic acid polymer. In some embodiments, the first polymer and/or the second polymer is a synthetic (i.e., non-naturally occurring) polymer. In some embodiments, the first polymer and/or the second polymer is a synthetic linear polymer.

In some embodiments, the complex is detected based on its conformation. In some embodiments, the complex is detected using gel electrophoresis. In some embodiments, the complex is detected using centrifuge force microscopy, optical tweezers, dynamic light scattering, or fluorescence.

In some embodiments, the sample is complex. In some embodiments, the sample is a urine sample. In some embodiments, the method detects an analyte that is present at less than 100 or less than 10 copies in a sample.

The foregoing embodiments apply equally to the various aspects provided herein, including those recited below. They are not repeated for the sake of brevity.

Another aspect of this disclosure provides a method for detecting an analyte in a sample comprising combining a sample with a plurality of polymers, each polymer conjugated to an analyte-specific binding partner, under conditions that allow binding of two or more analyte-specific binding partners to an analyte simultaneously, wherein two or more analyte-specific binding partners are able to bind to a single analyte simultaneously, and detecting a complex formed by the binding of the plurality of polymers or a subset of the plurality of polymers to a single analyte in the sample, wherein presence of the complex is indicative of presence of the analyte in the sample.

Another aspect of this disclosure provides a method for detecting an analyte in a sample comprising combining a sample with a first polymer and a second polymer, each conjugated to two or more analyte-specific binding partners, each analyte-specific binding partner conjugated to a single polymer having specificity for a different analyte, each polymer having a single analyte-specific binding partner for each analyte, under conditions that allow binding of the analyte-specific binding partners to their respective analytes, wherein binding partners having specificity for the same analyte are able to bind to a single analyte simultaneously, and detecting a complex formed by the binding of the first polymer and the second polymer to an analyte in the sample, wherein of the complex is indicative of presence of the analyte in the sample, and wherein the conformation of the complex is indicative of the identity of the analyte.

Another aspect of this disclosure provides a method for detecting one or more analytes in a sample comprising combining a sample with a plurality of polymer pairs, each polymer pair comprising a first and a second polymer, each conjugated to an analyte-specific binding partner for the same analyte, under conditions that allow binding of the analyte-specific binding partners to their respective analytes, wherein binding partners having specificity for the same analyte are able to bind to a single analyte simultaneously, and detecting a complex formed by the binding of a polymer pair to its respective analyte, and identifying the analyte by the conformation of the complex, wherein each polymer pair forms a complex having a unique conformation upon binding of its respective analyte.

In some embodiments, the locations of analyte-specific binding partners conjugated to first and second polymers are different between polymer pairs.

Another aspect of this disclosure provides a method for detecting an analyte in a sample comprising combining a sample with a polymer conjugated to two or more analyte-specific binding partners, under conditions that allow binding of each analyte-specific binding partner to an analyte, wherein the analyte-specific binding partners are able to bind to a single analyte simultaneously, cleaving one or more loops formed by the polymer upon binding of two or more analyte-specific binding partners to an analyte in the sample, thereby forming a cleaved complex, and detecting the cleaved complex, wherein presence of the cleaved complex is indicative of presence of the analyte in the sample.

In some embodiments, the method comprises combining the sample with a polymer conjugated to two analyte-specific binding partners, under conditions that allow binding of each analyte-specific binding partner to an analyte, wherein the analyte-specific binding partners are able to bind to a single analyte simultaneously, cleaving a loop formed by the polymer upon binding of the two analyte-specific binding partners to an analyte in the sample, thereby forming a cleaved complex, and detecting the cleaved complex, wherein presence of the cleaved complex is indicative of presence of the analyte in the sample.

In some embodiments, the loop is cleaved is enzymatically cleaved. In some embodiments, the loop is cleaved using a restriction enzyme. In some embodiments, the polymer comprises an enzyme cleavage site between two analyte-specific binding partners. In some embodiments, the polymer comprises an enzyme cleavage site between every two analyte-specific binding partners.

In some embodiments, the loop is cleaved is chemically cleaved. In some embodiments, the polymer comprises a chemically cleavable site between two analyte-specific binding partners. In some embodiments, the polymer comprises a chemically cleavable site between every two analyte-specific binding partners.

These and other aspects and embodiments of the invention will be described in greater detail herein.

BRIEF DESCRIPTION OF DRAWINGS

FIG. 1A illustrates that nucleic acid (e.g., DNA) constructs can be joined to form X-shaped structures in the presence of analytes or another targeted molecular interaction.

FIG. 1B illustrates that nucleic acid (e.g., DNA) X-shaped structures can be formed by cutting looped constructs. FIG. 1C shows that the formation of nucleic acid (e.g., DNA) X-shaped structures can be detected by gel electrophoresis, with greater separation than looped nucleic acid nanostructures. In this example, the polymers are nucleic acids in the form of DNA, the analyte is streptavidin, and the analyte-specific binding partners are biotin molecules. Arrows indicate the location of the gel bands created when the analyte (streptavidin) is present. Notably, in the absence of analyte, no corresponding gel band is formed. Significantly, the X-shaped complexes formed using the polymer pairs of this disclosure are able to separate significantly from the starting unbound polymers particularly as compared to separation achieved by looped structures.

FIG. 4A shows that using the same 1% agarose gel, running at 100V allows the X-shaped DNA to enter the gel and slowly migrate (arrow), while running at 200V does not facilitate migration of X-shaped DNA into the gel (arrow). FIG. 4B illustrates how gel electrophoresis can be used to separate X-shaped DNA (white arrow, bottom near loading wells) from linear DNA more cleanly than looped DNA (solid black arrow) from linear DNA by starting electrophoresis at a low voltage and then increasing it to a higher voltage.

DETAILED DESCRIPTION OF INVENTION

This disclosure provides new and surprisingly improved approaches to detect analytes and molecular interactions. Some of these approaches employ polymer pairs that are able to bind to an analyte, such as a single molecule or compound, or a multicomponent complex, thereby undergoing a conformational change from single, optionally linear, polymers to a polymer-analyte complex typically having an X-shaped structure, with four free ends, and an analyte bridge. Unexpectedly, the difference in structure between the bound and unbound (e.g., essentially linear) states allows for significantly better separation between bound and unbound states, as compared to other methods of the prior art. Moreover, these methods can be used to detect analytes with low noise, thereby allowing for sensitive detection of low abundance analytes. Various descriptions provided herein refer solely to analytes but it is to be understood that this is for the sake of brevity and that multicomponent complexes are also intended in such descriptions unless stated otherwise.

Figure 1A:
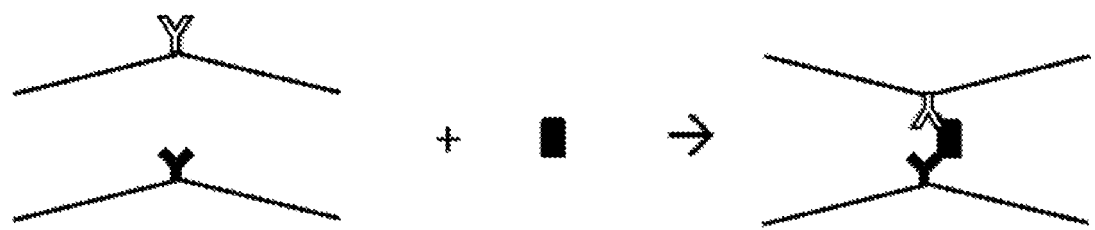
FIGS. 1A-C. Detection of molecular interactions using a nucleic acid (e.g., DNA) in an X-shaped topology.
Figure 2:
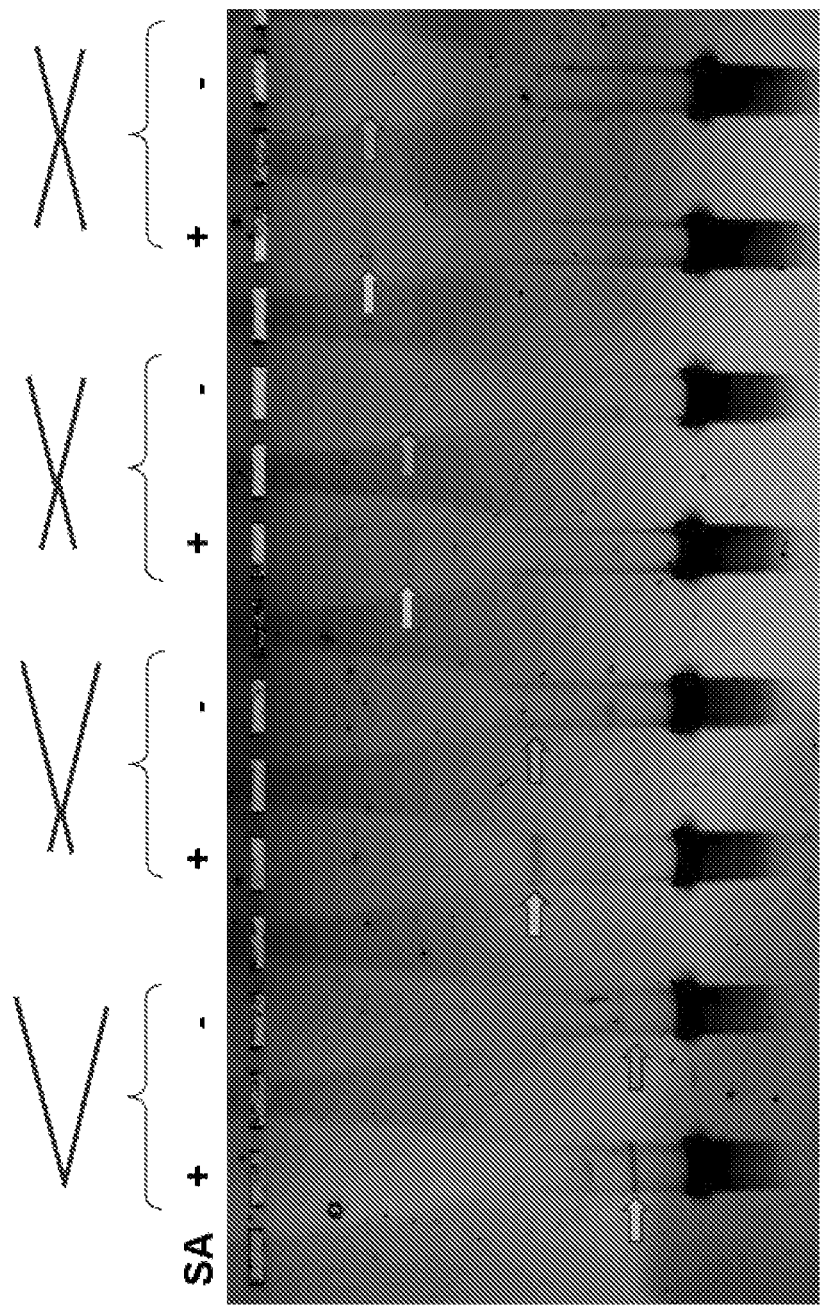
FIG. 2. Effect of binding partner and thus joining position on migration during gel electrophoresis. Illustrated are nucleic acid (e.g., DNA) constructs with single biotin modifications at different positions. These nucleic acid constructs are joined via binding to streptavidin. From left to right, the single modifications are located at the end, 630 bp from the end, 1950 bp from the end, and 3270 bp from the end of the 7308 bp M13 scaffold. The arrows indicate the bands created in the presence of streptavidin (left of the "+" lane) and not created in the absence of streptavidin (left of the "−" lane).

FIGS. 1A and B illustrate two basic approaches. The first approach shown in FIG. 1A uses a polymer pair (i.e., two polymers). Each polymer of the pair is conjugated to an analyte-binding partner. The Figure illustrates the use of an antibody as the analyte-specific binding partner. These analyte-specific binding partners may bind to the same analyte or to different components of the same multicomponent complex. If binding to the same analyte, the analyte-specific binding partners may or may not be identical (i.e., they may bind to the same epitope, provided the analyte has at least two copies of the epitope, or they may bind to different epitopes on the same analyte). Importantly, the binding partners must be capable of binding to the same analyte (or multicomponent complex) simultaneously in order to form the bridge between the two polymers of the polymer pair. The binding partners may be located anywhere along the length of the polymers, with the most pronounced separation from unbound polymers more likely to occur if they are located at about the mid-point of the polymer. However, as illustrated in FIG. 2, polymers having binding partners located at their ends or at other internal locations, once complexed, can also be distinguished from linear unbound polymers and perhaps more significantly can be distinguished from other complexes, thereby facilitating multiplexed assays.

Figure 1B:
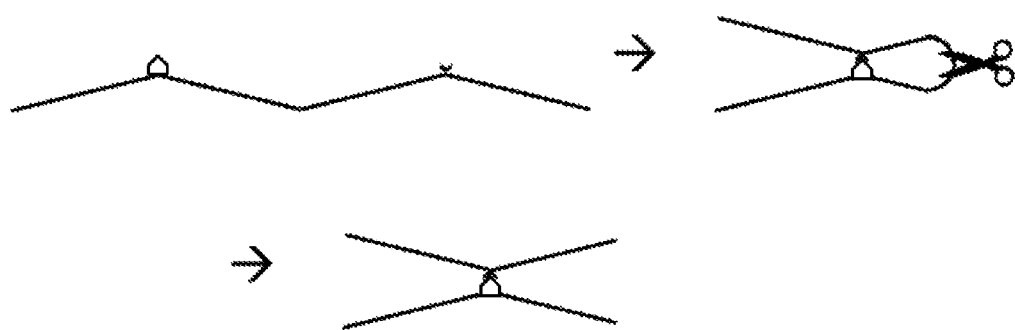
Figure 1C:
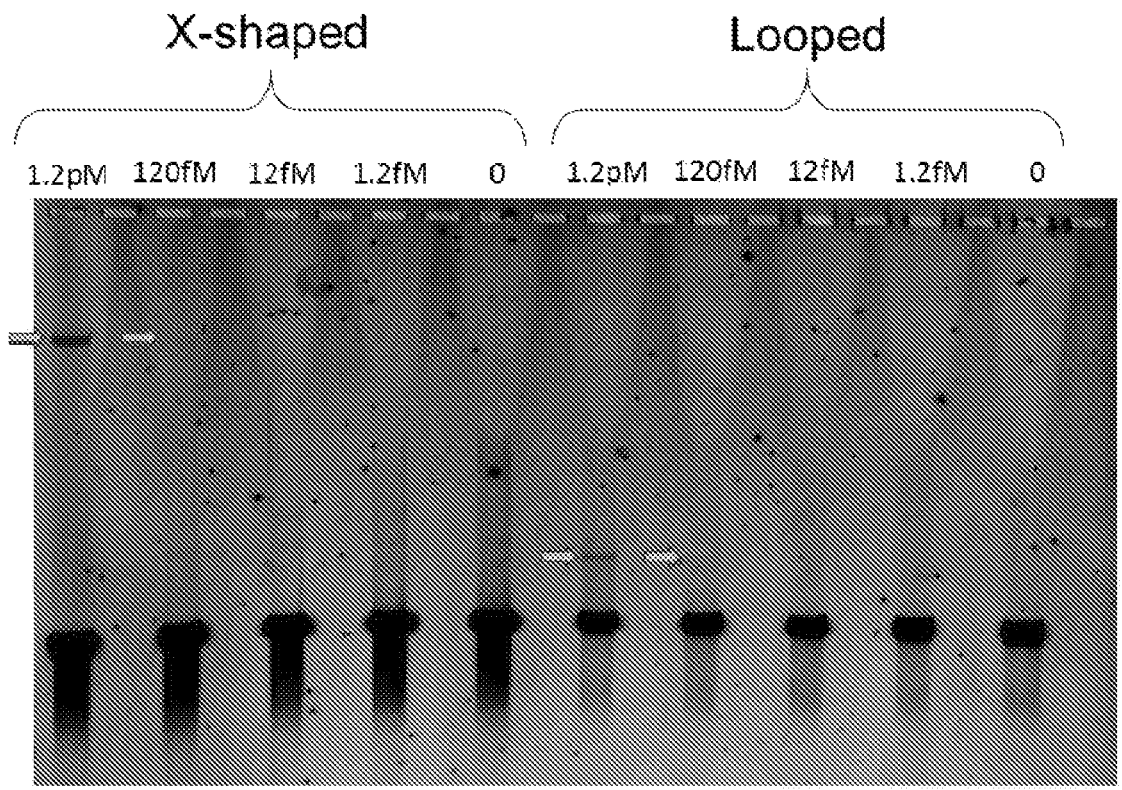
Figure 3:
FIG. 3. Effect on gel electrophoresis of a DNA nanoswitch cut using a restriction enzyme. A mixture of linear and looped forms of a DNA nanoswitch is incubated at 37° C. for 1 hour with (+) or without (−) the restriction enzyme PacI. The looped DNA nanoswitches are created with a DNA oligonucleotide bridge that binds to nucleotide regions 2414-2442 and 3931-3960 on the M13 scaffold. Pad has one restriction site at nucleotides 3116/3114 which exists in the looped region on the scaffold. The physical separation between the bridged and unbridged forms for the cut nanoswitch is 1.8 times that of the uncut nanoswitch.
Figures 4A, 4B:
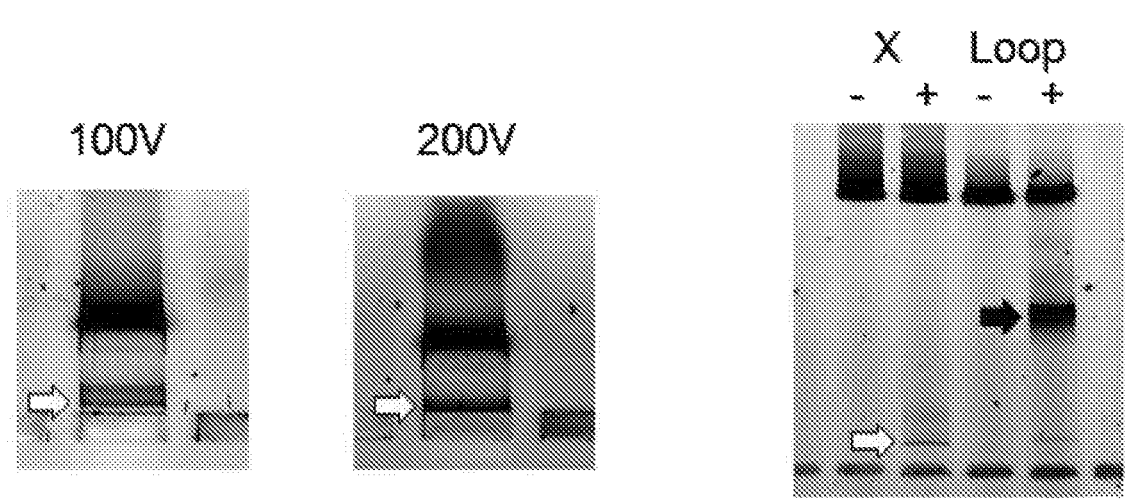
FIGS. 4A-B. Effect of gel running conditions on migration of DNA in an X-shaped topology.

The second approach shown in FIG. 1B uses a single polymer having conjugated thereto two analyte-specific binding partners. As in the first approach, these binding partners may bind to the same analyte or to different components of the same multicomponent complex. If binding to the same analyte, the analyte-specific binding partners may or may not be identical (i.e., they may bind to the same epitope, provided the analyte has at least two copies of the epitope, or they may bind to different epitopes on the same analyte). Importantly, the binding partners must be capable of binding to the same analyte (or multicomponent complex) simultaneously in order to form a loop structure from the polymer. The binding partners may be located anywhere along the length of the polymer, although the most pronounced separation from unbound polymers is more likely to occur if they are located at about one quarter and three quarters the length of the polymer, as illustrated. Binding of the two binding partners to the same analyte or multicomponent complex forms a looped structure, and this looped structure is cleaved by any known means to form an X-shaped structure similar to that of the first approach. Cleavage may be achieved chemically or enzymatically, although other means are not excluded. Cleavage can occur directly on the polymer (such as a restriction enzyme cutting a specific nucleotide sequence), or via a distinct entity connecting two polymer portions (such as using TCEP to cleave a disulfide bond connecting two nucleic acids). As shown in FIG. 3, cleavage increased the separation between nanoswitches that contain an interaction from those that are linear. Additionally, increasing the voltage during electrophoresis can cause X-shaped structures to enter the gel and then become significantly separated from the linear band, as illustrated in FIG. 4B.

This disclosure provides variations of these two approaches, including detection of more than one analyte using a single polymer pair, detection of more than one analyte using more than one polymer pair (with each pair specific for one analyte), identification of one or more analytes simultaneously with or following detection, and the like. This disclosure also contemplates additional mechanisms for bridging polymers in order to enhance or stabilize their binding, particularly when the binding affinity of the binding partner for the analyte is low or the target is a multicomponent complex which is easily disrupted. These and other variations are considered part of this disclosure and will be discussed in greater detail herein.

Detection of Analytes or Multicomponent Complexes

Some aspects of this disclosure provide methods for detecting the presence of an analyte of interest in a sample. These aspects use at least two binding partners that have specificity for the same analyte. The binding partners may be identical to each other, provided that they can both bind to the analyte simultaneously. As an example, they may be identical antibodies provided the antigen to which they bind has several epitopes that can be bound by the antibodies simultaneously without interference. The binding partners may be different from each other but have binding affinity for the same analyte. As an example, they may be antibodies that bind to different epitopes on the same antigen provided they can bind to the antigen simultaneously without interference. The X-shaped complex can be used to determine the presence of an analyte in a sample. If the analyte is present, the binding partners that are attached to the polymer(s) will bind to the analyte to form an X-shaped complex (or other detectable and distinguishable shape) or a closed loop conformation which is then cleaved to form an X-shaped complex (or other detectable and distinguishable shape). In the absence of the analyte, binding will not occur, and the polymers will not form either the X-shaped structure or the looped conformation (or other detectable and distinguishable shape).

As noted above, methods provided herein involve the formation of complexes as a result of analyte binding to analyte-specific binding partners that are conjugated to one or more polymers. In its simplest form, the disclosure contemplates a pair of polymers (a polymer pair, as used herein) in which each polymer is conjugated to a binding partner and the binding partners bind to the same analyte. In doing so, the polymers are connected to each other, with the analyte acting as the bridge between the two. The complex is referred to herein as an X-shaped complex for illustrative purposes, since if the analyte-specific binding partners are located at or near the mid-point the complex will effectively resemble an X shape. The end user need not observe the final shape that is adopted by the complex. Instead it is only necessary that the end user detect the complex and be able to distinguish it from other complexes. This may be accomplished using, for example, gel electrophoresis, in which case the complexes are visualized as separately migrating bands on a gel. It is the separate positions of the bands along the length of the gel that allows an end user to distinguish between complexes. It should therefore be apparent that the particular shape adopted by the complex that is formed upon analyte binding may vary, and may or may not comprise an X-shape, provided that the newly formed conformation (or shape) can be detected and distinguished from other conformations (or shapes). Thus, in designing polymers and determining placement of binding partners along the length of such polymers, one of ordinary skill will select polymers and placements that result in detectable complexes that can be distinguished from other complexes and from the starting materials. It is also be understood that while this disclosure refers to X-shaped complexes, the methods and products are not so limited as described above. The reference to X-shaped complexes is for brevity and convenience only and it is to be understood that the complexes may adopt other conformations upon analyte binding and still be useful provided that they are detectable and distinguishable.

The following protocol can be used to detect an analyte in a sample: 1) combine a sample with a polymer pair wherein each polymer in the pair comprises at least one binding partner of the analyte (e.g., antibodies specific to the analyte), and 2) determine the presence of a X-shaped complex or other conformation for example by gel electrophoresis. Detection of a X-shaped complex is an indication that the analyte is present in the sample and binds to the two binding partners bound to the polymer pair. As described herein, in other embodiments, the X-shaped complex can be resolved using single-molecule force probes, including but not limited to optical tweezers, magnetic tweezers, tethered particle motion, atomic force microscopy (AFM), centrifuge force microscope (CFM). In other embodiments, the X-shaped complex can be observed directly using single-molecule fluorescence imaging.

The following is another protocol that can be used to detect an analyte in a sample: 1) combine a sample with a polymer that comprises at least two binding partners specific for an analyte (e.g., antibodies specific to the analyte), 2) treat the polymer in order to cleave it via enzymatic or chemical means at a predetermined location, thereby forming either an X-shaped complex or two polymer fragment, and 3) determine the presence of a X-shaped complex for example by gel electrophoresis. Detection of a X-shaped complex is an indication that the analyte is present in the sample and binds to the two binding partners bound to the polymer. As described herein, in other embodiments, the X-shaped complex can be resolved using single-molecule force probes, including but not limited to optical tweezers, magnetic tweezers, tethered particle motion, atomic force microscopy (AFM), centrifuge force microscope (CFM). In other embodiments, the X-shaped complex can be observed directly using single-molecule fluorescence imaging.

Some methods detect and optionally quantitate a multicomponent complex. A multicomponent complex is a complex of two or more components. The components may be covalently linked to each other, or they may be non-covalently linked to each other. Examples of such complexes include transcriptional or translational complexes, cell cycle complexes, inflammasomes, and other "-some" like complexes. In these methods, the binding partners may recognize and bind to different components of the complex yet together they still bind to the sample complex. These methods rely on the association between the components of the complex to be sufficiently stable to withstand the binding reaction and the readout process (e.g., gel electrophoresis). If they are not, then a latch mechanism may be used to stabilize the interaction between the two polymers of a polymer pair or between the two binding partners on a single polymer.

Some aspects of the disclosure provide methods for screening a library of molecules or compounds based on their ability to be recognized and bound by the binding partners conjugated to the polymer pair or single polymer, as described above. For example, this method can be used to screen a DNA-encoded chemical library, such as a macrocycle library [4] for high-throughput, logic-gated compound screening. Screening of such a library also facilitates purification and identification of the putative lead candidates.

As will be understood based on this disclosure, the conformation of the complex can be used to identify the analyte. As described herein, the conformation may be visualized as a band of a particular migration in a gel electrophoresis readout, as an example.

Quantitation

The methods may be used not only to detect analytes but also to measure their level in a sample. Such quantitation assumes that the binding partners and polymers (or polymer pairs) are used in excess amounts and thus that the only limiting feature to forming X-shaped complexes is the presence and level of analyte.

The number of X-shaped complexes is therefore a readout of the number of analytes present in a sample since each complex forms due to the presence of a single analyte. If the readout means is gel electrophoresis, then intensity of the band formed by dye molecules bound to or attached to the polymers in an electrophoretic gel can be quantitated and used to measure analyte level. Alternatively, the band corresponding to X-shaped complexes can be extracted from the gel and quantified using sequencing, qPCR, or single-molecule imaging.

The methods provided herein may be used to detect analytes that are present in a sample at very low concentration including for example at millimolar, micromolar, nanomolar, picomolar, femtomolar, attomolar, zeptomolar or less.

Multiplexing

Multiplexed assays may be carried out in at least two different ways. In the first approach, each polymer or polymer pair specifically binds (via its analyte-specific binding partners) to a single analyte or a single multicomponent complex, and a plurality of polymers or polymer pairs are used to detect a plurality of analytes or multicomponent complexes. Each polymer or polymer pair is designed to generate an X-shaped complex (or other shaped complex) that is different and distinguishable from the X-shaped complexes formed by other polymers or polymer pairs upon binding of their respective analytes or multicomponent complexes. This is accomplished by varying the position of the binding partners bound to each polymer in a polymer pair, or varying the positions of the binding partners on the polymer to be cleaved. FIG. 2 demonstrates that varying the position of the binding partners in the polymer pair aspects results in different complexes that migrate to different extents in a gel electrophoresis readout. An end user can design each of the polymers in a polymer pair, or each polymer in a plurality of polymers, so that the each analyte of interest will form a unique complex with such polymers and its presence will not only be detected but also distinguished from the presence of all other analytes in the sample.

Each polymer pair or each polymer are designed to bind to only a single type of analyte or complex, and thus the polymers may be conjugated to 1, 2 or more binding partners, with all the binding partners specific for the analyte or the multicomponent complex. The binding partners for a first analyte, for example, may be located at the midpoint of each polymer of a polymer pair, and the binding partners for a second analyte, for example, may be located at one end of each polymer of a polymer pair, and the binding partners for a third analyte, for example, may be located at about 25% of the length of each polymer of a polymer pair. It is to be understood that the binding partners need not be placed at the same position on each polymer of a particular polymer pair (i.e., the binding partners in a polymer pair need not be similarly or identically positioned on polymers in the pair). However, they must be positioned so as to create a complex that is detectable and distinguishable from other complexes that may be formed and also from the starting material of uncomplexed (or linear, non-looped) polymers.

The positions of binding partners on a polymer, and thus the distances between such binding partners, will be dictated by the ability to distinguish between different complexes. The binding partners may be placed spaced apart by about 100, 200, 300, 400, 500, 600, 700, 800, 900, 1000, 1100, 1200, 1300, 1400 or 1500 nucleotides, or by greater numbers of nucleotides.

Based on the foregoing, one of ordinary skill in the art can readily contemplate the use of a plurality of polymer pairs, each of which bind to a different analyte, and detection of one or more or all analytes in a sample based, for example, on bands in a gel electrophoresis, with each band representing a given analyte and the intensity of each band correlated with the amount of complex and thus the amount analyte in the sample.

In the second approach, each polymer pair is able to bind more than one analyte or multicomponent complex and assume a different and distinguishable shape upon binding each different analyte or complex. Thus, rather than having a plurality of polymers or polymer pairs, one or a small number of such polymers or polymer pairs are required to detect a plurality of analytes. Here each polymer in a polymer pair will be conjugated to two or more binding partners, each binding partner specific for a different analyte or complex. Again the polymers in a polymer pair are designed such that they form a different and distinguishable complex for each analyte they bind, through their conjugated binding partners. Similarly, when a single polymer is used in the loop and cleavage applications, it will be designed to form a different and distinguishable complex for each analyte it binds. Typically the polymers in this approach will only bind to a single analyte at a given time even though each polymer is able to bind to two or more analytes, due to the high local analyte concentration created when the analyte is bound to the first binding partner, as compared to free analytes in solution. This phenomenon is particularly useful when the analyte concentration is low, such as may be the case with a limited copy analyte in a sample. As with the polymer pair approach, the binding partners for different analytes are positioned along the length of the polymer such that they adopt different looped conformations upon binding of each different analyte and then give rise to different X-shaped conformations following cleavage.

Both of these approaches have been shown to achieve better discrimination, higher sensitivity and signal-to-noise ratios, and also higher degrees of multiplexing.

Multiplexing can also be performed by utilizing polymers that are bound to different fluorescent dye molecules, either covalently or non-covalently, that can be distinguished by their different wavelengths of absorbance and/or emission. Multiplexing can also be performed by identifying unique sequences that correspond to specific polymer pairs binding specific analytes in the band corresponding to the X-shaped confirmation via qPCR or high-throughput sequencing.

Sample and Analytes

The sample being tested for the presence of the one or more analytes may be a biological sample such as a bodily fluid (e.g., a blood sample, a urine sample, a sputum sample, a stool sample, a biopsy, and the like). The sample may be complex. As used herein, a complex sample refers to a sample comprising a plurality of known and unknown components. The plurality may be in the tens, hundreds or thousands.

The analyte to be detected may be virtually any analyte provided binding partners specific for the analyte are available and that it can be bound by at least two binding partners simultaneously. This typically means that it is large enough to be bound by two binding partners and that it has at least two epitopes that can be bound simultaneously, whether those epitopes are identical or different from each other. The analytes may be or may comprise nucleic acids, peptides or proteins, carbohydrates, lipids, or any combination thereof.

In one illustrative example, the analyte may be a compound used to diagnose a particular condition in a subject such as but not limited to a human subject. For example, the analyte may be a marker of pregnancy such as Early Pregnancy Factor (EPF) which is released within hours of fertilization. The ability to detect EPF using the methods provided herein will therefore lead to a more sensitive determination of pregnancy at early time points post-fertilization. It may also be used to assess infertility in a subject. Thus, in some embodiments, the analyte will be EPF (or other pregnancy markers), the analyte-specific binding partners will be specific for EPF and may be antibodies or antigen-binding antibody fragments that bind to EPF, and the polymers may be nucleic acids such as DNA. The polymers may or may not have cleavable linkers between the locations of the two binding partners.

Polymers

The polymers may be naturally occurring polymers or non-naturally occurring polymers. They may be or may comprise nucleic acids, peptides, proteins, polysaccharides, lipids, and the like. They may be or may comprise block polymers or block-co-polymers.

The polymers may be nucleic acids in whole or in part. They may comprise naturally occurring nucleotides and/or non-naturally occurring nucleotides. They may be or may comprise DNA, RNA, DNA analogs, RNA analogs, PNA, LNA and combinations thereof, provided it is able to hybridize in a sequence-specific manner to oligonucleotides and/or to be conjugated to a binding partner.

In some instances, the polymers are single-stranded nucleic acids. Such nucleic acids may be modified to include one or more binding partners at particular positions.

The polymers may be single stranded nucleic acids hybridized to one or more modified oligonucleotides that are conjugated to one or more binding partners. Such nucleic acids may be referred to herein as scaffold nucleic acids. They may also be referred to as "single-stranded" and it is to be understood that this refers to their state prior to hybridization to the one or more oligonucleotides. The scaffold nucleic acid may be hybridized to one or more including two, three, four, or more oligonucleotides. Each oligonucleotide may comprise one or more binding partners, depending on their length. As an example, if a nucleic acid is conjugated to two binding partners, the nucleic acid may be hybridized to one oligonucleotide comprising the two binding partners or it may be hybridized to two oligonucleotides, each of which comprises a binding partner. The oligonucleotides are typically designed to hybridize to particular regions on the scaffold, such as at about the mid-point of the scaffold. The scaffold nucleic acid may or may not be hybridized to additional, unmodified oligonucleotides.

Accordingly, the polymer may be a single-stranded nucleic acid, a partially double-stranded nucleic acid, or a completely double-stranded nucleic acid. The polymer may be a double-stranded nucleic acid. For example, it may be at least 10%, at least 20%, at least 30%, at least 40%, at least 50%, at least 60%, at least 70%, at least 80%, at least 90%, at least 95%, at least 96%, at least 97%, at least 98%, at least 99%, or 100% double-stranded. The nucleic acids may therefore comprise double-stranded and single-stranded regions. Double-stranded regions may comprise "single-stranded nicks" as the hybridized oligonucleotides may not be ligated to each other.

When the polymer is a nucleic acid, it may be of any length sufficient to visualize the nucleic acid and the resultant complex it forms in the presence of analyte, and in some instances to form a loop upon binding to analyte. In some instances, the nucleic acid is at least 1000 nucleotides in length, and it may be as long as 20,000 nucleotides in length, or it may be longer. The nucleic acid may be 1000-20,000 nucleotides in length, 2000-15,000 nucleotides in length, 5000-12,000 in length, or any range therebetween. The nucleic acid may be a naturally occurring nucleic acid (e.g., M13 DNA such as M13mp18 having a length of about 7250 nucleotides). Use of M13 DNA as a scaffold nucleic acid is disclosed by Rothemund 2006 Nature 440:297-302, the teachings of which are incorporated by reference herein. The disclosure contemplates use of full length M13 DNA or use of a fragment of M13 DNA provided it is of sufficient length.

Nucleic acids to be used as polymers may be naturally occurring and thus harvested from a naturally occurring source. Alternatively, they may be non-naturally occurring nucleic acids such as polymerase chain reaction (PCR)-generated nucleic acids, rolling circle amplification (RCA)-generated nucleic acids, etc. If the polymer is a single stranded nucleic acid, it may be generated using for example asymmetric PCR. Alternatively, double-stranded nucleic acids may be subjected to strand separation techniques in order to obtain the single-stranded nucleic acids.

It is to be understood that the nucleic acid may also comprise a plurality of nicks that are typically located between bound oligonucleotides. The length and the number of oligonucleotides used may vary. In some instances, the length and sequence of the oligonucleotides is chosen so that each oligonucleotide is bound to the scaffold nucleic acid at a similar strength. This is important if a single condition is used to hybridize a plurality of oligonucleotides to the nucleic acid. In some instances, the oligonucleotides are designed to be of approximately equal length. The oligonucleotides may be about 10, about 15, about 20, about 30, about 40, about 50, about 60, about 70, about 80, about 90 or about 100 nucleotides in length. The number of oligonucleotides in the plurality may be about 50, about 60, about 70, about 80, about 90, about 100, about 110, about 120, about 130, about 140, about 150, about 160, about 170, about 180, about 190, or about 200, without limitation.

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides. It will be understood that the number of oligonucleotides will depend in part on the application, the length of the scaffold, and the length of the oligonucleotides themselves.

Binding Partners

The binding partners may include without limitation antibodies including but not limited to single chain antibodies, antigen-binding antibody fragments, antigens (to be used to bind to their antibodies, for example), receptors, ligands, aptamers, aptamer receptors, nucleic acids, small molecules, and the like.

The linkage between the polymer (e.g., nucleic acid) and the binding partner may be covalent or non-covalent depending on the strength of binding required for a particular application.

The sample is combined with a polymer pair or with a polymer (conjugated to analyte-specific binding partners) under conditions that allow binding of analyte-specific binding partners to their respective analytes if present in the sample. Those conditions may vary depending on the nature of the analyte and the binding partner. Those conditions may also take into consideration the stability of the polymer, binding partner and/or analyte. In some embodiments, the conditions may comprise a temperature at about 4° C., between 4-25° C., a pH between 5.5-7, and a physiological salt concentration. The temperature may be between 4-10° C., between 10-15° C., between 15-20° C., between 20-25° C., or about room temperature. The conditions may comprise inhibitors such as DNase inhibitors, RNase inhibitors, or protease inhibitors.

Manufacturing Methods

If the polymer is a nucleic acid hybridized to one or more oligonucleotides, it may be generated by first incorporating a reactive group (or moiety) into the oligonucleotide, preferably at or near one of its ends, and then reacting this group (or moiety) with the binding partner of interest which may or may not be modified itself. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Examples of reactive groups that non-covalently conjugate to other molecules (leading to a reversible conjugation) include biotin and avidin or streptavidin reactive groups (which react with each other), antibody (or antibody fragment) reactive groups and antigens, receptors and receptor ligands, aptamers and aptamer ligands, nucleic acids and their complements, and the like. Virtually any reactive group may be used, provided it participates in an interaction of sufficient affinity to prevent dissociation of the binding partner from its oligonucleotide.

In another example, protein binding partners can be coupled to single oligonucleotides by expressing the protein with a single tag, such as SNAP-tag, or sortase-recognized LPETG. Alternatively, one can use non-specific amine or cysteine reactive chemistry, along with an oligonucleotide that is modified with an affinity purification tag that can be used to isolate proteins that only have one oligonucleotide/tag attached, as has previously been described [4].

Background signal can be further reduced, after hybridization, by separating out constructs with only a single M13 bound to a single protein from constructs that have two M13 scaffolds joined to a single protein using gel electrophoresis.

Chemical or Enzymatic Cleavage

In embodiments described herein that involve formation of looped conformations upon analyte binding, it is contemplated that such loops will be cleaved through any variety of cleaving mechanisms. Such polymers are designed to comprise cleavable linkers at regions between binding partners. The cleavable linkers may be located at virtually any position between two binding partners in the region that will form the loop upon analyte binding, provided that once cleaved the complex can be detected and distinguished from other complexes so formed by binding to a different analyte.

Thus, schematically, the binding partners and the cleavable linkers may be ordered as follows:

- -BP1 - - - cleavable linker - - - BP2- -, where BP1 and BP2 represent a first and a second binding partner that bind to the same analyte. In the presence of the appropriate analyte, BP1 and BP2 bind to the analyte and thereby form a loop that comprises the cleavable linker. Upon cleavage of the cleavable linker, the linear polymer is converted to an X-shaped complex reminiscent of the complex formed when two physically separate polymers are bound together through a common analyte.

The term cleavable linker refers to a compound that may or may not be identical in nature to the remaining polymer and that ultimately is specifically cleaved. The polymer may comprise one or more cleavable linkers such as a chemically cleavable linker, a photo-cleavable linker, and an enzymatically cleavable linker or sequence.

In some embodiments, the cleavable linker is a chemically cleavable linker. In such embodiments, one or more moieties and/or sites in the linker may be cleaved and/or degraded by various chemicals and/or reaction conditions (e.g., specific pH or change in pH). As a non-limiting example, the chemically cleavable linker may comprise a hydrazone species that can be cleaved in an acidic environment. Hydrazone species refer to a class of organic compounds with the structure $R_1R_2C\!=\!\!NNH_2$.

This structure is illustrated below:

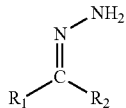

Hydrazone species are readily degraded under acidic conditions (e.g., pH about 5-6). Various hydrazone species may be used in the cleavable linkers of the present disclosure. For instance, in some embodiments, $R_1$ and/or $R_2$ may be derived from alkyl, acyl, benzophenone, methyl, ethyl, ester, ether and other similar functional groups. In more specific embodiments, the hydrazone species can include, without limitation, acyl hydrazones, benzophenone hydrazones, acetone hydrazones, N,N-dialkylhydrazones, and the like.

Other linker cleavable by various chemical stimuli are as follows:

| Cleavage Stimuli | Cleavable Group | Examples | Ease of Cleavage (min) |
|---|---|---|---|
| Acidic reagents | P-methoxybenzyl, phosphoramidate, acetal, hydrazone, t-butylcarbamate, Trityl, substituted trityl (DMT) | DMT cleaved with mild acid (pH ~5) | 90 sec e.g., DMT |
| Basic reagents | Cyanoethylgroup, sulfone, hydrazone, acylhydrazone, acylhydrazone | N-alkylation acylsulfonamide cleave rapidly in minutes in NaN$_3$. | <2 |
| Reducing reagents | Disulfide bridges, azo compounds | Azo (5 mM Na$_2$S$_2$O$_4$, buffer, pH-7.4, RT); TCEP:NH$_4$HCO$_3$ (8:2) | <5 (azo) |

Other chemically cleavable moieties can also be used in the chemical linkers of the present disclosure, as known by persons of ordinary skill in the art and may be available from commercial sources such as Glen Research and Ambergen. In addition, reference can be made for example to published US applications US20150361422, US20150099650 and US20130004523.

In some embodiments, the cleavable linker is a photo-cleavable linker. In such embodiments, one or more moieties in the linker may be cleaved and/or degraded by photolysis. In various embodiments, the photolysis may be initiated by any photon with sufficient energy to affect the chemical bonds of the linker. Non-limiting examples of such photons include visible light, uv light, x-rays, and gamma rays.

In some embodiments, the cleavable linker is a enzymatically cleavable linker. In such embodiments, one or more moieties in the linker may be cleaved and/or degraded by various enzymes. Of particular interest are restriction endonucleases that cleave nucleic acids in a sequence-dependent manner. It is this sequence dependence that allows an end user to control the specific location at which a loop will be cleaved to form an X-shaped complex (or other cleaved complex).

Latching Mechanism for Stability and/or Detection of Weak Interactions

The disclosure further provides that the polymers are capable of maintaining an X-structure or a looped conformation (prior to cleavage) even in the absence of an analyte or in the presence of a weakly bound analyte. In order to accomplish this, the polymers may comprise a "latch". The latch is an additional binding interaction that occurs between polymers of a polymer pair or within a polymer (for the looped and cleaved approach), only once the binding partners have bound to the analyte or multicomponent complex. The latching mechanism is only possible when the two or more latch components come within sufficient physical proximity to each other, and this only occurs once analyte is bound by the binding partners. The latch can serve to stabilize, including to essentially "freeze", an existing X-shaped complex or looped conformation, regardless of whether the analyte or multicomponent complex remains in place. These latches are contemplated for use, inter alia, in the detection of low or single copy analytes or multicomponent complexes.

The latches can be chemical or DNA-based latches.

A variety of different types of latches are contemplated, including direct and indirect latches, covalent and non-covalent latches, externally-triggered and self-triggering latches, amplifying latches, protectable latches, and reversible latches. Furthermore, these different categories of latches can be combined in various combinations (e.g. one could create an indirect, non-covalent, externally-triggered latch) for different applications.

In some instances, the latch maintains the X-shaped complex or the looped conformation throughout the entire detection method, including for example during gel electrophoresis. It is contemplated that the gel electrophoretic conditions may not be optimal for the binding of the analyte and the analyte-specific binding partner, and thus that this binding interaction may be unstable during gel electrophoresis. In that instance, the presence of the latch binding interaction serves to stabilize the complex, before or after cleavage, and notably throughout the gel electrophoresis or any other desired detection approach regardless of whether the analyte and binding partner interaction is maintained during that step. It is to be understood that the latch binding interaction may be used in a similar manner to address any instability of the analyte—binding partner interaction as a result of a changed condition during the various steps of the detection methods.

Direct and Indirect Latching

One approach for "welding shut" X-shaped structures and/or looped conformations to facilitate readout using gel electrophoresis is to directly cross-link the interacting molecules of interest to each other. "Direct latching" can be accomplished using, for example, a cross-linker such as (succinimidyl 4-(Nmaleimidomethyl) cyclohexane-1-carboxylate) (SMCC) or glutaraldehyde, to crosslink, for example, and amine to a sulfhydryl group, or two amines to each other, respectively. If reactive groups desired to form a cross-link are not native to the molecules of interest, these molecules can be engineered directly to facilitate direct cross-linking.

An alternative strategy to direct cross-linking that may provide greater flexibility and modularity is an "indirect latching" approach. In this case, the molecules or molecular regions being cross-linked to each other to "weld shut" the X-shaped structures and/or looped conformations are not directly part of the molecules of interest, but are instead attached to the polymer, adjacent or near to the attachment points of the two molecules being assayed. In such a system, the molecules of interest can be exchanged or replaced with alternative molecules without having to develop a different latch system. The latch will still create a similar-sized loop as in direct latching.

In some embodiments, hybrid systems can also be created, in which one part of the molecular latch is directly connected to or a part of the molecules of interest, whereas the other part is connected to the polymer.

Covalent Vs Non-Covalent Latches

Latch closure can occur through the formation of a either a covalent or non-covalent bond. Examples of non-covalent interactions that could be used to stabilize loop closure include DNA hybridization, receptor-ligand bond formation (e.g. between biotin and streptavidin), and formation of interactions between DNA and proteins. Examples of covalently cross-linked latches include glutaraldehyde latches, click chemistry latches, and sortase latches.

Ligase Latching

In one embodiment, a covalent latch is contemplated. That latch involves the covalent ligation of the two nucleic acid strands. In the case of target nucleic acid detection, the 3' overhang and the 5' overhang (which are the unhybridized regions of the "detector" strands) can be ligated to each other once bound to a target nucleic acid. Since ligase (e.g., T4 ligase) typically only repairs DNA nicks if the opposing strand is present, this scheme should covalently link the two ends of the detector strands only when the target strand is hybridized to the polymer. The 3' overhang will have an intact 3' hydroxyl and the 5' overhang will have a 5' phosphate, both of which are required for certain ligases. The polymer so generated will therefore incorporate a detector strand having a 5' overhang having a 5' phosphate. The ligation procedure could be carried out to "freeze" the states of the polymer or polymer pair. Additionally or alternatively, the ligated X-shaped structure could be heated to release the analyte, enabling it to react with another analyte and for the cycle to be repeated, as described above in the context of an amplifying X-shaped complex. The process can be repeated multiple times to increase the number of X-shaped complexes that read out in the presence of the target nucleic acid. This allows for detection of even a single copy of the analyte.

For nucleic acid (e.g., DNA and RNA) detection at low levels, detector strands could be intentionally designed to be weakly interacting so that the "catch and release" activity could be easily exploited to amplify the signal from such targets. Signal amplification may occur in at least two different ways: one in which there is a linear amplification that is dictated by the number of "catch and release" cycles, and one in which the amplification is stochastic due to weakly interacting target sequences naturally binding and unbinding with the detector strands and their 3' and 5' overhangs.

In the case of linear amplification using cyclic catch and release, in one instance, the interaction would be designed to be stable at the ligation temperature (typically 4° C. to RT), but unstable at slightly elevated temperatures. In this approach, the binding partners hybridize the analyte nucleic acids at low temperature, the detector strands are ligated to each other, the temperature is increased to dissociate the analyte nucleic acid from the binding partner, and the process is repeated with another polymer conjugated to a binding partner. The process may be repeated one or more time. It is expected that the amplification would be roughly linear with the number of cycles performed, since each target nucleic acid has a new chance to react at each cycle. This can potentially enable quantitative detection at low levels since the number of cycles can be controlled (for example, by using a thermal cycler). In the simplest embodiment, the ligase may be present in the sample throughout all of the cycles, and the temperatures would be limited to temperatures at which the ligase does not substantially degrade.

It will be apparent based on this disclosure that a similar approach can be taken even if the analyte is not a nucleic acid. In these instances, the analyte may be a protein or another moiety and the X-shaped complex is designed to measure a binding interaction with that analyte. Such binding interaction may occur using protein based binding partners such as but not limited to antibodies, antibody fragments, binding peptides, and the like. The invention contemplates that the X-shaped complex will additionally contain a latch comprising two detector strands (one having a 3' overhang and one having a 5' overhang), wherein the detector strands only come into sufficient proximity to each other and thus are able to bind a trigger nucleic acid when the first binding interaction occurs. The detector strands and their respective overhangs would be designed to be sufficiently close to the binding partners used to capture the target of interest, so that when the loop is closed (as a result of the first binding interaction) the overhangs are in close proximity. An additional nucleic acid, referred to herein as a trigger or latch nucleic acid, having complementarity to the 3' and 5' overhangs, is then allowed to hybridize to the overhangs, and the overhangs can then be ligated to each other in the presence of a ligase. This trigger or latch nucleic acid could be added at a certain desired time or could be included in the mixture with the polymer or polymer pair. Additionally, the ligase could be added at a desired time or included with the mixture. It will be understood that the 3' overhang comprises a 3' hydroxyl and the 5' overhang comprises a 5' phosphate.

Strong Interaction Latching

In another embodiment, the loops are latched closed by using two nearby moieties that strongly interact with each other. In this case, the latching either needs to be triggered by an external reagent or kinetically trapped so that the moieties are unlikely to spontaneously react with each other unless held in close proximity for a prolonged time. One example is a nucleic acid overhang that interacts strongly with another nucleic acid overhang but only weakly with itself.

For example, two interacting overhangs can each be designed to interact strongly with the other through base pairing, but to also interact weakly with itself (i.e., internally) through base pairing to form hairpins. In this case, the hairpins act as a kinetic trap to prevent spontaneous association of the two strands, but when in close proximity for a prolonged time the likelihood of the overhangs interacting together is increased due to the natural breathing of the hairpin and the insertion of the other overhang. The relative energies of the hairpins and of the binding interactions between the overhangs can be tuned by changing the number of bases involved in each type of interaction.

In order to facilitate the detection and characterization of a wide range of molecular interactions, provided herein are a collection of methods for holding X-shaped complexes in the closed or looped state. These latches are designed to only close, when a transient interaction occurs between two molecules that are in the same locations on the scaffold as the latch components.

When no transient interaction occurs, the latch is designed to not close. Currently, interactions that are not strong enough to keep X-shaped complexes closed during gel electrophoresis are difficult to measure and detect. By developing "latch" systems capable of keeping X-shaped complexes shut even when the primary interaction is weak, the range of molecules and molecular interactions that can be studied using X-shaped complexes can be expanded. Uses for the latch system include, but are not limited to, detection of analytes by stabilizing an X-shaped complex or a loop formed by a sandwiching assay with two detection antibodies attached to the polymers, stabilizing of interactions between members of a compound library and target molecules for drug discovery/screening and purification of molecules through a separation assay. These applications and the required latch designs are described in greater detail herein.

Externally Triggered Vs Self-Triggering Latches

Latch formation (e.g. cross-linking) could be triggered externally via the introduction of molecules, or via photoactivation, force application, heating, change in solution conditions, changes in the concentration or presence of ions or atoms in solution etc.

Alternatively, the latches could exist in a metastable state which could be triggered to enable latching as a result of some molecular event, for example, transient bond formation between the weak interacting molecules of interest.

Amplifying Latches

In order to amplify the detection signal, latches can be designed so that each antigen could set off multiple latches, resulting in the closure of more than one X-shaped complex. This would be a natural application of the self-triggering latches, in which the transient formation of a bond between the molecule of interest and molecules on the scaffold (e.g. two antibodies that can bind the analyte simultaneously as in a sandwich assay) and trigger the formation of a latch. In such a system, the analyte could detach from the X-shaped complex to trigger the formation of additional latches without compromising the closure of the initial latch. An alternative design for an amplifying latch would be to have multiple different types of latches, such as master and slave latches. In this case, binding of the analyte to a master latch would cause the release of multiple components (e.g. DNA strands) that could then trigger the closure of multiple slave latches to enable amplification of the signal. If latches were designed to be both masters and slave a chain reaction could result.

Protectable Latches

Protective groups can be used to reduce non-specific and unwanted interactions between the latch system and molecules of interest. For example, in the case of DNA latches, this can be accomplished through the use of protection strands that could hybridize to the DNA latch anchor components then be removed via strand displacement. These protection strands could either be separate molecules of DNA, or part of the original latch anchors (e.g. they could have self-complementary components).

"Deprotection" or activation of the latch system could either be performed as a separate step, or as part of a latch triggering event. Deprotection could occur via photoactivation, DNA strand displacement, DNA cleavage, chemical cleavage or any of the triggering mechanisms described herein.

Reversible Latches

Latches can be designed to be reversible, e.g. reopened using strand displacement, enzymatic cleavage, photoactivation (e.g. azobenzene can be switched between two different states by photoactivation, with one state stabilizing DNA hybridization, and the other state destabilizing DNA hybridization), photocleavage or force.

Pre-Latching

There are instances when one may wish to latch before mixing with a sample. Reversible latches could be used to hold two components close to one another while a second binding interaction occurs. For example, if two halves of an aptamer are used to bind a single analyte, the latch can be used to hold the two halves of the aptamer in close proximity, such that when the analyte, to which the aptamers bind, is present the two halves of the aptamer can bind to the analyte. One would then want to break the initial latch, and potentially form another latch to stabilize the loop while running.

Detection Mechanism

The newly formed complexes between binding partners and analytes can be detected in a variety of ways including but not limited to gel electrophoresis. When gel electrophoresis is used, a transition from an unbound conformation to a complex may be determined by a change in migration distance. Other ways of detecting transition between unbound and bound conformations include but are not limited to optical tweezers, magnetic tweezers, tethered particle motion, a centrifuge force microscope as described in published PCT patent application WO2011/153211, atomic force microscopy (AFM), and light microscopy. Still other approaches contemplated by the disclosure include directly detecting changes in length using single molecule fluorescence imaging, detecting changes in the average rheological properties of a solution of the complexes of the invention, and monitoring changes in hydrodynamic radius using dynamic light scattering.

The complexes may be visualized in any number of ways depending on the nature of the analyte and/or the polymer. For example, if the polymer is DNA-based, then the complex can be visualized by staining with nucleic-acid specific stains, such as but not limited to SYBR Gold. If the analyte or polymer is a protein or is peptide-based, then the complex may be visualized by staining with protein-specific stains such as but not limited to Coomassie Blue. Stains that emit in the visible range may be preferred for some embodiments. It is contemplated that in some instances the polymer is visualized instead of the analyte. This is particularly the case when the polymer is much larger than the analyte. In some instances using gel electrophoresis to separate the complexes, the gel may be impregnated with stains such as SYBR Gold or Coomassie Blue. Such gels are provided by ThermoFisher, for example.

Post-Detection Processes: Gel Extraction, Sequencing and/or PCR

This methods can also be used in conjunction with gel extraction or elution and sequencing, single molecule imaging, or PCR for detection. Thus, the methods may further comprise purifying analytes from samples or from the X-shaped complexes themselves. The X-shaped complexes can be physically separated from linear polymers that are not bound by analytes using gel electrophoresis. And more significantly, the analytes bound to the X-shaped complexes can be physically separated from the sample. Thus, in some embodiments, the disclosure contemplates the capture and purification of proteins or other analytes of interest using the methods provided herein. Targets of interest can be extracted from fluid, then isolated and/or purified from other components in a reaction mixture or sample.

This method of separation uses two analyte-specific binding partners and thus is more specific and more stringent than traditional purification utilizing only a single binding partner (such as a single antibody). This is because both binding partners need to bind the analyte of interest in order for X-shaped complex formation to occur. This is in contrast to prior art methods that typically rely on a single binding partner for detection.

As an example, in order to purify analytes a polymer pair with two analyte-specific capture antibodies and optionally latch oligonucleotides can be used. The polymer pair is contacted with a sample, binding is allowed to occur, the latch is allowed to close (e.g., by the introduction of a crosslinker or a trigger or latch nucleic acid), and the mixture is then run on a gel.

Using a latch system will increase the yield of the purification, since for purification the analyte need only stay bound to a single antibody, instead of both. The latch will keep the local concentrations high, allowing for rebinding during gel purification, in the event the analyte dissociates from only a single antibody. The analyte-polymer complex can be purified from the gel using electroelution, and the analyte can be separated from the polymer complex, potentially by adding another ligand to saturate the antibodies, or through a change in pH.

In still another embodiment, if the analyte is not a protein but the analyte-specific binding partners are proteins, then the method may comprise a step of removing the analyte-specific binding partners. For example, if protein-based binding partner is used such as an antibody or an antibody fragment, and the polymer is a nucleic acid, then the method may include a DNAse digestion to remove the polymer and a protease digestion to remove the protein based binding partner. Then the target could be further purified for example by liquid chromatography, if desired.

Products Including Kits

Also provided herein are the polymers, polymer pairs, and kits comprising polymers or polymer pairs. The polymers may be conjugated to binding partners of interest or they may be provided with binding partners of interested with or without the reagents required to conjugate the two. Thus, for example, in some embodiments, a polymer conjugated to two binding partners which bind to the same analyte is provided. In some embodiments, two polymers each conjugated to a binding partner, wherein both binding partners bind specifically to the same analyte. In still other embodiments, provided are oligonucleotides that are bound to binding partners of interest and "scaffold" nucleic acids to which such oligonucleotides hybridize in a sequence specific manner to form one version of the polymers of this disclosure.

REFERENCES

1. Halvorsen K, Schaak D, Wong W P (2011). Nanoengineering a single-molecule mechanical switch using DNA self-assembly. Nanotechnology. 22(49):494005.
2. Koussa M A, Halvorsen K, Ward A, Wong W P. (2015) DNA nanoswitches: a quantitative platform for gel-based biomolecular interaction analysis. Nat Methods. 12(2): 123-126.
3. Gartner Z J, Tse B N, Grubina R, Doyon J B, Snyder T M, Liu D R (2004). DNA-templated organic synthesis and selection of a library of macrocycles. Science. 305(5690): 1601-1605.
4. Howarth M, Chinnapen D J, Gerrow K, Dorrestein P C, Grandy M R, Kelleher N L, El-Husseini A, Ting A Y (2006) A monovalent streptavidin with a single femtomolar biotin binding site. Nat Methods. 3(4):267-73.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for detecting an analyte in a sample comprising
   combining a sample with a first polymer and a second polymer, wherein the first polymer is physically separate from the second polymer, and each is conjugated to an analyte-specific binding partner, under conditions that allow binding of analyte-specific binding partners to respective analytes, wherein the analyte-specific binding partners are able to bind to a single analyte simultaneously,
   detecting a complex formed by the binding of both the first polymer and the second polymer to an analyte in the sample, through their respective analyte-specific binding partners, wherein presence of the complex is indicative of presence of the analyte in the sample,
   wherein the first and second polymers are not bound to each other directly or indirectly in the absence of the analyte, and
   wherein the analyte is a peptide, protein, carbohydrate, lipid or combination thereof.

2. The method of claim 1, wherein the analyte-specific binding partners conjugated to the first and second polymers are identical.

3. The method of claim 1, wherein one or both of the analyte-specific binding partners are antibodies or antigen-binding antibody fragments.

4. The method of claim 3, wherein the analyte-specific binding partners bind to different epitopes of an analyte.

5. The method of claim 1, wherein the analyte-specific binding partner conjugated to the first polymer is located at about the mid-point along the length of the first polymer and/or the analyte-specific binding partner conjugated to the second polymer is located at about the mid-point along the length of the second polymer.

6. The method of claim 1, wherein the first polymer and/or the second polymer is a nucleic acid.

7. The method of claim 1, wherein the first polymer and/or the second polymer comprise naturally occurring nucleotides.

8. The method of claim 1, wherein each of the first polymer and the second polymer is a single-stranded nucleic acid.

9. The method of claim 1, wherein each of the first polymer and the second polymer is a partially double-stranded nucleic acid.

10. The method of claim 9, wherein each of the first polymer and the second polymer comprises a single-stranded nucleic acid hybridized to one or more oligonucleotides.

11. The method of claim 1, wherein each of the first polymer and the second polymer is a completely double-stranded nucleic acid.

12. The method of claim 11, wherein each of the first polymer and the second polymer is a completely double-stranded nucleic acid having nicks in at least one nucleic acid strand.

13. The method of claim 1, wherein the complex is detected based on its conformation.

14. The method of claim 1, wherein the complex is detected using gel electrophoresis, centrifuge force microscopy, optical tweezers, dynamic light scattering, or fluorescence.

15. The method of claim 1, wherein the sample is a urine sample.

16. The method of claim 1, wherein the method detects an analyte that is present at less than 100 or less than 10 copies in a sample.

17. The method of claim 1, wherein each of the first and second polymers is conjugated to two or more analyte-specific binding partners, and each analyte-specific binding partner conjugated to a single polymer has specificity for a different analyte.

18. The method of claim 1, wherein conformation of the complex identifies the analyte.

19. The method of claim 1, wherein the analyte is a multicomponent complex.

20. The method of claim 19, wherein the analyte-specific binding partners bind to different components of the multicomponent complex.

21. A method for detecting one or more analytes in a sample comprising
combining a sample with a plurality of polymer pairs, each polymer pair comprising a first and a second polymer, each conjugated to an analyte-specific binding partner for the same analyte, under conditions that allow binding of the analyte-specific binding partners to their respective analytes, wherein binding partners having specificity for the same analyte are able to bind to a single analyte simultaneously,
detecting a complex formed by the binding of a polymer pair to its respective analyte, and identifying the analyte by the conformation of the complex, wherein each polymer pair forms a complex having a unique conformation upon binding of its respective analyte and wherein each first and each second polymer in a pair are not bound to each other directly or indirectly in the absence of the respective analyte.

* * * * *